(12) United States Patent
Anferov

(10) Patent No.: US 9,452,300 B2
(45) Date of Patent: Sep. 27, 2016

(54) SYSTEMS AND METHODS OF CONTROLLING A PROTON BEAM OF A PROTON TREATMENT SYSTEM

(71) Applicant: ProNova Solutions, LLC, Knoxville, TN (US)

(72) Inventor: Vladimir Anferov, Bloomington, IN (US)

(73) Assignee: ProNova Solutions, LLC, Knoxville, TN (US)

( * ) Notice: Subject to any disclaimer, the term of this patent is extended or adjusted under 35 U.S.C. 154(b) by 0 days.

(21) Appl. No.: 14/491,061

(22) Filed: Sep. 19, 2014

(65) Prior Publication Data

US 2015/0080633 A1   Mar. 19, 2015

Related U.S. Application Data

(60) Provisional application No. 61/879,942, filed on Sep. 19, 2013.

(51) Int. Cl.
    *A61N 5/00*     (2006.01)
    *A61N 5/10*     (2006.01)

(52) U.S. Cl.
    CPC ..... *A61N 5/1077* (2013.01); *A61N 2005/1087* (2013.01)

(58) Field of Classification Search
    USPC .......................................... 250/492.1, 492.3
    See application file for complete search history.

(56) References Cited

U.S. PATENT DOCUMENTS

| | | | |
|---|---|---|---|
| 7,317,192 B2 | 1/2008 | Ma | |
| 7,372,053 B2 | 5/2008 | Yamashita et al. | |
| 7,381,979 B2 | 6/2008 | Yamashita et al. | |
| 7,560,715 B2 | 7/2009 | Pedroni | |
| 7,961,844 B2 | 6/2011 | Takeda et al. | |
| 8,269,198 B2 | 9/2012 | Dilmanian et al. | |
| 2007/0284548 A1 | 12/2007 | Kaiser et al. | |
| 2011/0101236 A1 | 5/2011 | Cameron et al. | |
| 2012/0224667 A1 | 9/2012 | Cheng et al. | |
| 2012/0280150 A1* | 11/2012 | Jongen | 250/492.3 |
| 2014/0121442 A1 | 5/2014 | Matteo et al. | |

FOREIGN PATENT DOCUMENTS

WO   WO2011036254   3/2011

OTHER PUBLICATIONS

Patent Cooperation Treaty, Int'l Search Report; Form PCT/ISA/210; Date of Mailing Dec. 30, 2014.

* cited by examiner

*Primary Examiner* — Nicole Ippolito
*Assistant Examiner* — Hanway Chang
(74) *Attorney, Agent, or Firm* — Pitts & Lake, P.C.

(57) ABSTRACT

Systems and methods of controlling a proton beam in a proton therapy system, the system including a proton beam delivery system including at least one achromatic beamline having a first power setting to direct a proton beam having a first predetermined range of proton beam energies to a target treatment area, and a second power setting to direct a proton beam having a second predetermined range of proton beam energies to the target treatment area, and a power changing unit configured to control an energy level of the proton beam and a power setting of the at least one achromatic beamline such that the power changing unit changes the power setting of the at least one achromatic beamline between the first power setting and the second power setting based on changes in proton beam energy that occur within the first predetermined range of proton beam energies.

9 Claims, 3 Drawing Sheets

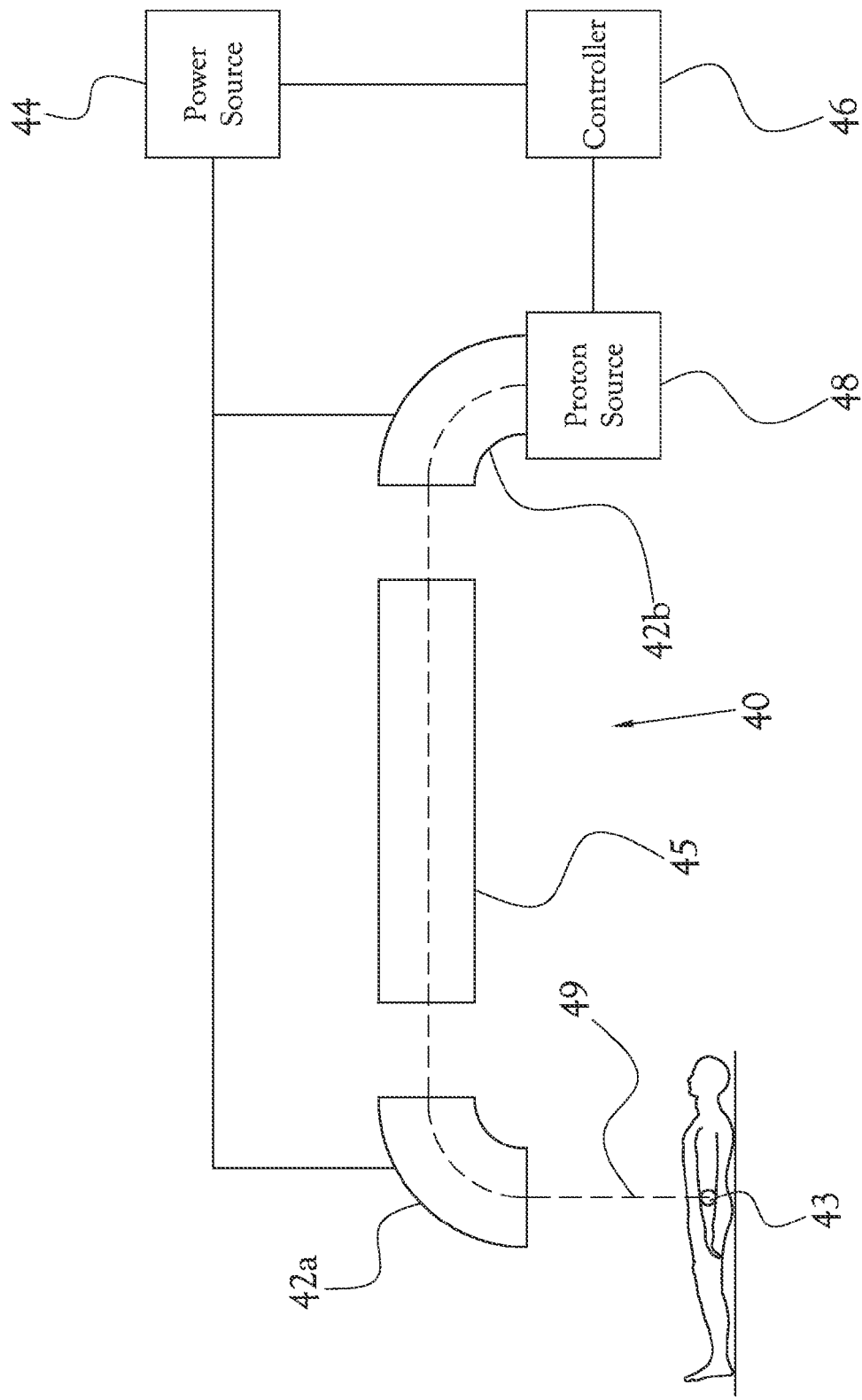

SYSTEMS AND METHODS OF CONTROLLING A PROTON BEAM OF A PROTON TREATMENT SYSTEM

CROSS-REFERENCE TO RELATED APPLICATIONS

This application claims the benefit of U.S. Provisional Patent Application Ser. No. 61/879,942, filed on Sep. 19, 2013, the disclosure of which is incorporated herein in its entirety by reference.

FIELD OF INVENTION

The present general inventive concept relates to proton therapy for cancer treatment, and, more particularly, to systems and methods of controlling a proton beam during proton therapy treatment of a patient.

BACKGROUND

Proton Therapy (PT) is a cancer treatment technology that uses high energy protons to penetrate a patient's body and deposit energy into treatment volumes such as cancerous tumors. The charged protons may be generated in a particle accelerator, commonly referred to as a cyclotron and/or a synchrotron, and directed to the patient in the form of a beamline using a series of magnets that guide and shape the particle beamline such that the particles penetrate the patient's body at a selected location and are deposited at the site of the treatment volume. Particle therapy leverages the Bragg Peak property of charged particles such that the majority of the energy is deposited within the last few millimeters of travel along the beam path —at a point commonly referred to as the isocenter, as opposed to conventional, intensity modulated radiation therapy (i.e., photons) in which the majority of energy is deposited in the first few centimeters of travel, thereby undesirably damaging healthy tissue.

Particle therapy treatment facilities typically consist of a single cyclotron and a plurality of treatment rooms. Thus, the single cyclotron is often adapted to generate a particle beamline that is then selectively directed to one of the various treatment rooms. A particle therapy treatment may include the selection of a desired energy level for the beamline, such that the energy of the particles is deposited substantially at the desired location (i.e., the treatment volume) inside the patient's body. Therefore, the energy level selection is directly related to the position and shape of the treatment volume within the patient's body. Frequently, the cyclotron will generate a standard high-energy proton beam, which may then be selectively modified as desired for the particular treatment protocol.

The beamline may be directed immediately to the patient without the need for any redirection. However, a more common approach is to redirect the beamline using a series of cooperating bending magnets which route the beamline to a proton nozzle mounted on a gantry. FIG. 1 illustrates an example embodiment prior art particle therapy gantry designed to receive and redirect a particle beamline to a patient. As illustrated, the particle therapy gantry 21 includes at least three bending magnets 11A-C to redirect the particle beamline 15 to the gantry's treatment nozzle 13, and eventually the patient 9 positioned on a treatment bed 17. This allows the beamline 15 to be selectively directed to the patient 9 from any angle and permits a physician to design a treatment plan that minimizes undesirable effects on healthy tissue. Stated differently, gantries are frequently adapted to rotate about a patient, and redirect the beamline to be perpendicular to the gantry's axis of rotation 19, illustrated by the directional arrow 19' in FIG. 1. Thus, the treatment nozzle 13 and beamline 15 may be rotated about the patient 9 such that the beamline 15 is able to penetrate the patient's body at a plurality of locations and encounter the treatment volume from multiple directions. This minimizes adverse effects on healthy tissue and increases the efficacy of the treatment.

Thus, in comparison to standard x-ray therapy, proton therapy is capable of significantly improving dose localization by increasing the dose delivered to the target volume, while minimizing the dose delivered to the surrounding tissue. These improvements are based on the finite penetration range of therapeutic proton beam in the target material. Furthermore, energy deposition to the target material increases as the proton beam slows down and reaches maximum energy near the end of the penetration range. The penetration depth and the location of the energy deposition peak (the Bragg peak) are defined by the proton beam energy. Therefore, a proton beam of a given energy delivers a therapeutic dose of energy at a specific treatment depth. In order to deliver this therapeutic dose to a target with a given extent in depth, proton beams with several different energies can be used.

To provide these several different energies, older proton therapy systems typically changed the proton beam energy in the treatment nozzle by inserting plates of material that attenuate the proton beam energy by the specified amount. More advanced conventional systems change the beam energy further upstream near the proton accelerator itself. Such conventional systems typically require a change of the beam transport line to match each subsequent proton beam energy.

Thus, a proton therapy system in which proton beam energies can be changed while reducing such structural changes and adjustments as described above would be desirable.

BRIEF SUMMARY

The present general inventive concept, in various example embodiments, includes a superconducting proton delivery system including a gantry wheel to rotate a proton beam nozzle around a target area of a patient. In some embodiments, the proton delivery system includes a system of achromatic bends which allow changing the beam direction for particles with different energies while using identical settings, enabling a proton beam of different energies (within an energy acceptance window of the achromatic beamline) to be transported through an achromatic beamline without changing the beamline settings.

Example embodiments of the present general inventive concept can be achieved by a proton delivery system for use in proton therapy, including at least one achromatic beamline having a first power setting to direct a proton beam having a first predetermined range of proton beam energies to a target treatment area, and a second power setting to direct a proton beam having a second predetermined range of proton beam energies to the target treatment area, and a power changing unit configured to control an energy level of the proton beam and a power setting of the at least one achromatic beamline such that the power changing unit changes the power setting of the at least one achromatic beamline between the first power setting and the second power setting based on changes in proton beam energy that occur within the first predetermined range of proton beam energies.

The power changing unit can be configured to change the power setting of the at least one achromatic beamline to reach the second power setting as the proton beam energy transitions from the first predetermined range of proton beam energies to the second predetermined range of proton beam energies.

The power changing unit can be configured to change the power setting of the at least one achromatic beamline between the first power setting and the second power setting based on a rate of change of the proton beam energy. The power changing unit can be configured to incrementally change the energy levels of the proton beam and/or the power settings of the at least one achromatic beamline.

The power changing unit can change the power setting of the at least one achromatic beamline while the proton beam energy is constant within the first predetermined range of proton beam energies.

The power changing unit can change the power setting of the at least one achromatic beamline simultaneously with a change in the proton beam energy within the first predetermined range of proton beam energies.

The first and second predetermined ranges of proton beam energies can be mutually distinct and non-inclusive of one another.

The at least one achromatic beamline can include a third power setting to direct a third predetermined range of proton beam energies to the target treatment area, and the controller is configured to incrementally change the power setting of the at least one achromatic beamline between the second and third power settings based on changes in the proton beam energies that occur within the second predetermined range of proton beam energies.

Example embodiments of the present general inventive concept can also be achieved by providing an achromatic beam transport system for use in proton treatment, including a superconducting achromat having a power setting defining an energy acceptance window such that the achromat directs a proton beam having a predetermined range of proton beam energies to a targeted area, the energy acceptance window having a minimum energy level and a maximum energy level, and a power changing unit configured to control an energy level of the proton beam and a power setting of the superconducting achromat such that the power changing unit changes the power setting of the superconducting achromatic based on changes in proton beam energy that occur between the minimum energy level and the maximum energy level.

The achromat can be configured as a superconducting achromat to direct the proton beam having a predetermined range of proton beam energies through the achromat without beam losses.

The achromat can be configured to transport the proton beam having a predetermined range of proton beam energies through the achromat to a targeted treatment volume having a predetermined depth without adjusting the power setting of the achromat.

Example embodiments of the present general inventive concept can also be achieved by providing a method of delivering a proton beam to target area of a patient in a proton therapy system, including utilizing an achromatic beamline having a first power setting to direct a first predetermined range of proton beam energies to a target treatment area, and a second power setting to direct a second predetermined range of proton beam energies to the target treatment area, changing an energy level of the proton beam between the first and second predetermined ranges of proton beam energies, and changing the power setting of the achromatic beamline between the first power setting and the second power setting based on changes in the proton beam energies that occur within the first predetermined range of proton beam energies.

The method may further include changing the power setting of the achromatic beamline to the second power setting as the proton beam energy transitions from the first predetermined range of proton beam energies to the second predetermined range of proton beam energies.

The operation of incrementally changing the power setting of the achromatic beamline can be based on a rate of change of the proton beam energy.

The achromatic beamline can include a third power setting to direct a third predetermined range of proton beam energies to the target treatment area.

The method can further include incrementally changing the power setting of the achromatic beamline between the second and third power settings based on changes in the proton beam energies that occur within the second predetermined range of proton beam energies.

Additional features and embodiments of the present general inventive concept will be set forth in part in the description which follows, and, in part, will be obvious from the description, or may be learned by practice of the present general inventive concept.

BRIEF DESCRIPTION OF THE FIGURES

The following example embodiments are representative of example techniques and structures designed to carry out the objects of the present general inventive concept, but the present general inventive concept is not limited to these example embodiments. In the accompanying drawings and illustrations, the sizes and relative sizes, shapes, and qualities of lines, entities, and regions may be exaggerated for clarity. A wide variety of additional embodiments will be more readily understood and appreciated through the following detailed description of the example embodiments, with reference to the accompanying drawings in which:

FIG. 4 illustrates a proton beam delivery system according to an example embodiment of the present general inventive concept.

DETAILED DESCRIPTION

Figure 1:
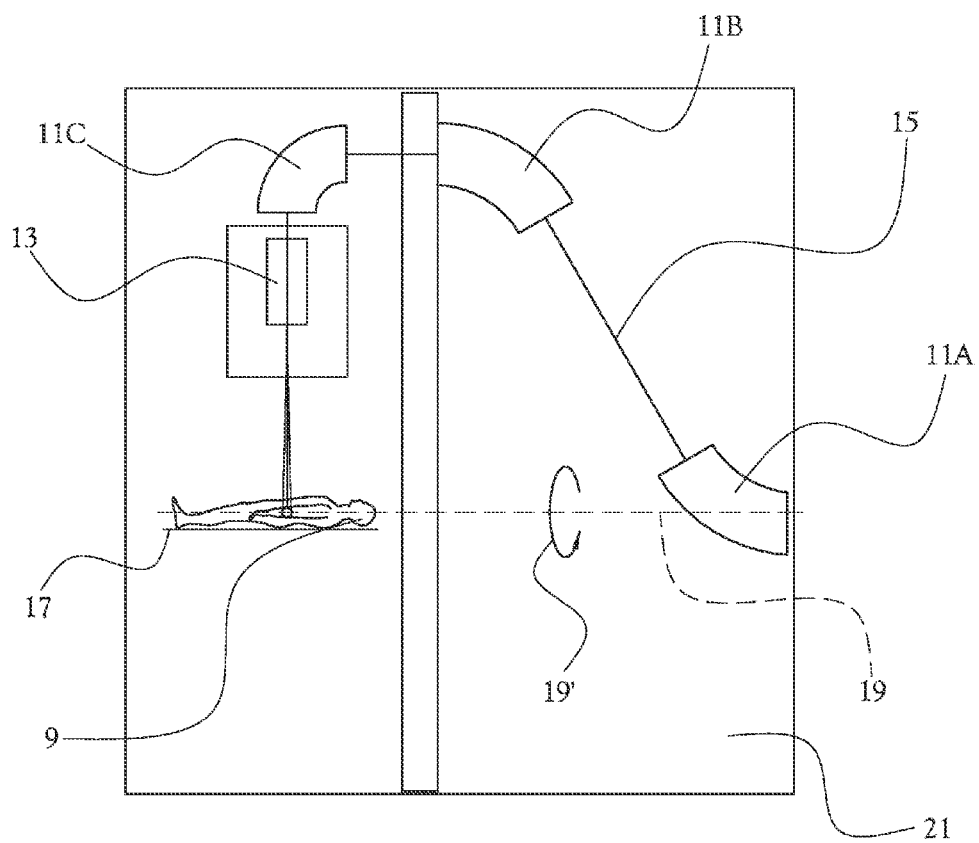
FIG. 1 illustrates an example embodiment of a prior art particle therapy system designed to receive and redirect a particle beamline to a patient.

Reference will now be made to the example embodiments of the present general inventive concept, examples of which are illustrated in the accompanying drawings and illustrations. The example embodiments are described herein in order to explain the present general inventive concept by referring to the figures.

The following detailed description is provided to assist the reader in gaining a comprehensive understanding of the structures and fabrication techniques described herein. Accordingly, various changes, modification, and equivalents of the structures and fabrication techniques described herein will be suggested to those of ordinary skill in the art. The progression of fabrication operations described are merely examples, however, and the sequence type of operations is not limited to that set forth herein and may be changed as is known in the art, with the exception of operations necessarily occurring in a certain order. Also, description of well-known functions and constructions may be omitted for increased clarity and conciseness.

Note that spatially relative terms, such as "up," "down," "right," "left," "beneath," "below," "lower," "above," "upper" and the like, may be used herein for ease of description to describe one element or feature's relationship to another element(s) or feature(s) as illustrated in the figures. Spatially relative terms are intended to encompass different orientations of the device in use or operation in addition to the orientation depicted in the figures. For example, if the device in the figures is turned over or rotated, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Various example embodiments of the present general inventive concept provide a system and method of delivering proton therapy treatment to a patient in which a sliding energy window of a proton beam may be utilized to reduce changes in beam transport lines, changing of attenuating plates, and so on. Thus, the various example embodiments described herein provide a more convenient method of changing proton beam energies during proton therapy.

Various example embodiments of the present general inventive concept may utilize a superconducting gantry design, which allows for a smaller and/or lighter gantry system due to the smaller components used in the superconducting system. Such superconducting systems may operate more optimally without the heat, eddy currents, etc., that may result from large current changes typically used to change the power of the beamline including the bending magnets in an achromat when altering the magnets' power for directing a proton beam of a different strength or energy level to a precise targeted area of the patient.

According to example embodiments of the present general inventive concept, a proton therapy system can include a proton delivery system including a superconducting gantry design using achromatic bends that enable a proton beam having a predetermined range of different energies to be transported through the achromatic beamline having bending magnets without changing the power provided to the bending or other directing beam-directing magnets, thus keeping the same power setting to redirect the proton beam as the energy level of the proton beam changes (within the predetermined range). Embodiments of the present general inventive concept thus provide a proton delivery system having a predetermined range of "acceptable" proton beam energies that can be accommodated by a fixed setting of the achromatic bending magnets to accurately deliver a proton beam to a targeted region of interest. Thus, there is an "energy acceptance window" which includes the range of energies, and therefore a corresponding range of depths of treatment, for which the bending magnet settings need not be changed. Once the proton beam energy is changed beyond the predetermined range of energies that can be accommodated by a given setting of the bending magnet system, a change in the current of the bending magnets is required to alter the path of the beamline to maintain accuracy of the beamline direction. This change in the current of the bending magnet system can cause unwanted heat and/or eddy currents which may be problematic, especially in a superconducting magnet system in which the superconducting components are kept at extremely low temperatures.

Various example embodiments of the present general inventive concept provide a system in which the power of the bending magnets, and thus the current provided to the bending magnets, can be changed in incremental phases as the energy of the beamline is altered within the acceptance window so that the heat and other eddy current problems associated with changes in power to the magnets are reduced or minimized. By changing the power of the bending magnets incrementally as the energy of the proton beam changes incrementally within a given energy acceptance window of the bending magnets, a sliding energy window is provided which reduces the magnitude of power changes to the bending magnets as the energy of the proton beam is changed. This allows the power to the bending magnets to be incrementally changed as the energy of the proton beam is changed within a given energy acceptance window, instead of waiting for the proton beam energy to reach the end of a given energy acceptance window before adjusting the power to the bending magnets to redirect the proton beam having entirely different energy levels.

Conventionally, changes to the power setting of the bending magnets occurs when the proton beam energy reaches the end of a given energy acceptance window. This can create unwanted heat and eddy currents in the bending magnets, and can negatively impact proton beam accuracy and treatment when larger tumors having a depth greater than the depth obtainable by a given energy range of the proton beam is desired.

In some embodiments, the present general inventive concept provides a superconducting bending magnet design to direct a proton beam to a treatment volume. The use of achromatic bends enables the proton delivery system to redirect the proton beam similarly for particles with different energy. As a result, a proton beam having a predetermined range of energies (i.e., within a predetermined energy acceptance window) can be transported through such an achromatic beam line without changing the beamline settings. Thus, smaller tumors having a depth that falls the depth that can be treated by a given range of proton beam energies within the energy acceptance window of the bending magnet setting can be treated without changing the power to the bending magnet system. For example, such achromatic systems can perform treatment on targets with small extent in depth (up to 5 cm) at fixed settings of the beamline. For larger targets having a greater extent in depth than can be treated by a given energy acceptance window, the system may gradually adjust the bending magnet settings to change the energy acceptance window during treatment so as to avoid sudden, abrupt changes in the bending magnet power that would otherwise be required by conventional systems to treat larger tumors. Such bending magnet power changes do not need to be perfectly synchronized with the switching of the energy of the proton beam, but may be done proportionately or incrementally to optimize the magnitude and/or quantity of changes to the bending magnet power based on desired performance and/or demands of a particular treatment program.

The achromatic beam transport of the present general inventive concept allows delivering a proton beam for radiation therapy without significant beam losses in the presence of energy spread in the incoming beam, and delivery of treatments with small extent in depth with static settings of the beamline. The achromatic beam transport system according to various example embodiments of the present general inventive concept can be changed slowly to adjust their energy acceptance window to cover dose delivery to targets with large extent in depth.

Various example embodiments of the present general inventive concept include a superconducting proton delivery system for treating a growth, treatment area, etc., in a patient using a proton beam having different energy ranges without changing the bending magnet settings in the achromat. That is, the growth may be treated with different energies using the same bending magnet steering settings within a predetermined range of proton beam energies. The range of acceptable energies of the proton beam that may be used at the same bending magnet settings is referred to herein as the energy acceptance window of a given bending magnet setting. Thus, if all of the energies that are needed to treat a growth fall within a single energy acceptance window, the bending magnets, or beamline direction settings, may remain static for the duration of the treatment. In some embodiments, the energy acceptance window will allow treatment to depths within a certain range, such as, for example 5 cm, without changing the bending magnet settings.

Figure 2:
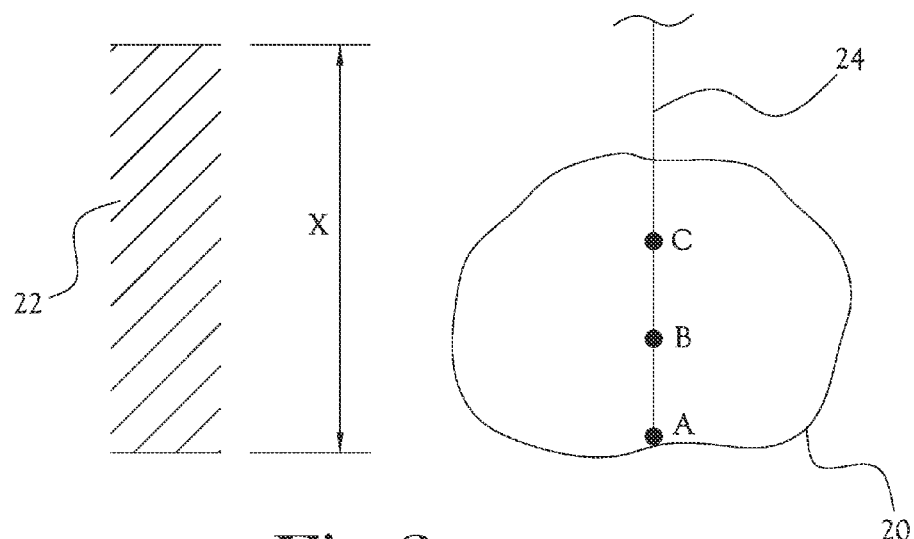
FIG. 2 illustrates a proton therapy treatment according to an example embodiment of the present general inventive concept.

FIG. 2 illustrates a superconducting proton therapy treatment configured in accordance with an example embodiment of the present general inventive concept. As illustrated in FIG. 2, a growth 20 in a patient is subjected to the proton beam. For purposes of illustration, it is predetermined that the energy acceptance window 22 for the superconducting proton therapy system of this example embodiment has a range of Xcm, as illustrated in FIG. 2. As the depth of all points of the growth 20 is within the range of the energy acceptance window 22, the beamline will not have to be changed during the therapy. In other words, the beamline direction settings, e.g., the current supplied to the bending magnets in the achromat, will not have to be changed since the energy range of the proton beam can be adjusted to treat the full depth of the tumor without changing the bending magnet power. Thus, as illustrated in FIG. 2, the proton beam 24 may be applied at a first energy to treat a depth at point A, a second energy to treat a depth at point B, a third energy to treat a depth at point C, and so on without any change in the beamline settings. It is understood that the points A, B, and C are chosen arbitrarily for ease of explanation and illustration of the elements of FIG. 2, and that other depth points obviously exist in the growth 20 as well as the energy acceptance window 22. In this case, the power of the bending magnets will not have to be changed for any proton beam 24 energy adjustments for the treatment of the growth 20.

It is noted that the points A, B, and C illustrated in FIG. 2 have been simplified for ease of understanding of the present general inventive concept, as the changing of the proton beam 24 energies may occur at different increments during the treatment. Also, the beam may be scattered horizontally, relative to the illustration in FIG. 2, to treat all areas of the growth 20. Nonetheless, due to the depth of the growth 20 being less than the range of energy levels in the energy acceptance window 22, the beamline settings may remain unchanged.

Figure 3:
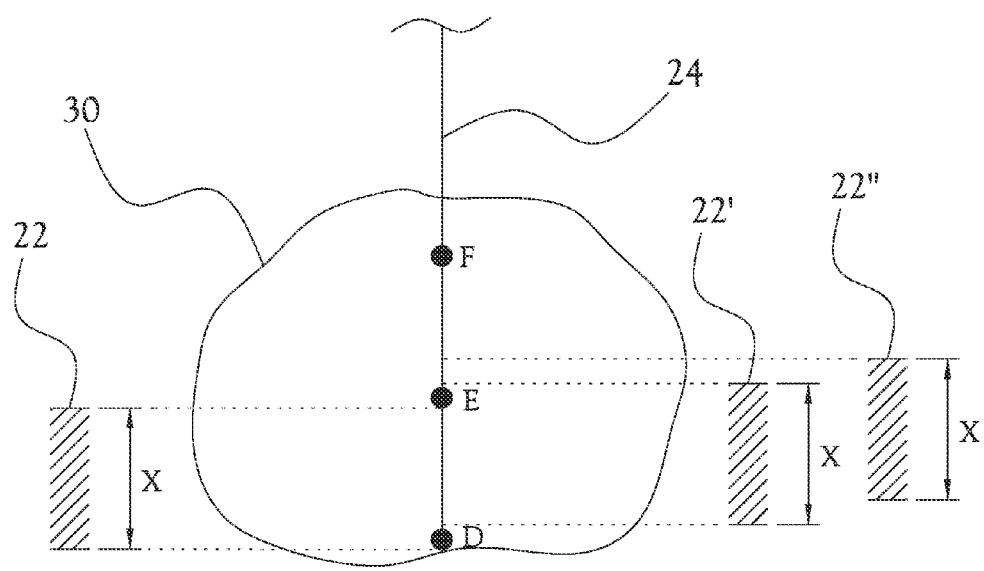
FIG. 3 illustrates a proton therapy treatment according to another example embodiment of the present general inventive concept.

FIG. 3 illustrates a proton beam delivery system according to another example embodiment of the present general inventive concept. In the example embodiment illustrated in FIG. 3, a growth 30 to be treated with the proton beam has a greater depth than the predetermined energy acceptance window 22 of the bending magnets. As illustrated in FIG. 3, the energy acceptance window 22 allows for static beamline settings for the bottom X units of measure (e.g., mm, cm, etc., according to the predetermined energy acceptance window settings of the achromat) of the growth 30. The equivalent points of the bottom of the growth 30 and the start of the energy acceptance window 22 have been chosen for ease of illustration, and it is understood that the bottom of the growth 30 may correspond to different points in the energy acceptance window 22, depending upon the beamline settings. Therefore, it would be possible to use the static beamline settings corresponding to the energy acceptance window 22 for point D of the proton beam 24, as well as X units of measure above point D. However, if the beamline settings are kept static for that entire range of depth, and thus not changed until the treatment at the depth of point E, which is outside the initial energy acceptance window 22, then a relatively large and sudden change in the current supplied to the bending magnets to change the bending magnet settings may cause unwanted heat, eddy currents, etc., which may have an adverse effect upon the components of the proton therapy system and treatment accuracy and quality. Therefore, rather than maintaining the static beamline settings for the energy acceptance window 22 for the entirety of the depths associated with that range, the bending magnet settings may be changed in small increments such that the energy acceptance window 22 "slides" corresponding to changes in the proton beam 24 energy.

In other words, after the energy of the proton beam 24 is adjusted to go to points just above point D, the bending magnet settings may be slightly changed so that the new energy acceptance window 22' corresponds to a range just above point D. The energy acceptance window 22' may cover the same range of distance from bottom to top as does the energy acceptance window 22, but will correspond to at least slightly different depths of the growth 30 as illustrated in FIG. 3. As the energy of the proton beam 24 is further adjusted to provide therapy to more shallow depths of the growth 30, such as approaching point E, the bending magnet settings may be incrementally changed again to produce the energy acceptance window 22", as illustrated in FIG. 3. The process may be repeated as the proton beam 24 energy is adjusted to treat point F and above. In other words, the energy acceptance window 22 may be adjusted so as to slide along with the adjusted energy of the proton beam 24. It is understood that while this description discusses changing the bending magnet settings after the treatment at point D, the changes may come before, or at the same time as the proton beam 24 energy changes, while keeping the range of the energy acceptance window so that it includes the current point of therapy. Because the range of depths included in the energy acceptance window is larger than the single depth at which proton therapy is currently taking place, it is not necessary that the beamline direction changes are synchronized with the beam energy setting. In other words, the beamline direction changes do not have to correspond at all points with the energy changes of the proton beam, due to the larger range of acceptable depths in the energy acceptance window.

FIG. 4 illustrates a proton beam delivery system for use in a proton therapy system according to an example embodiment of the present general inventive concept. As illustrated in FIG. 4, the proton delivery system 40 includes one or more achromatic bends 42a, 42b to redirect a proton beam 49 from a proton source 48, through a beamline 45, to a target area 43 of a patient. The achromatic bends 42a, 42b are connected to a power source 44 to provide power settings to the bending magnets of the achromats. A controller 46, also referred to as a power changing unit, can be provided to change the power settings applied to the achromatic bends. The power changing unit 46 can also be connected to the proton source 48 to change the energy level of the proton beam 49 generated by the proton source 48. The changes to the power settings and/or the energy levels can be made incrementally, based on relative rates of change of one to the other, proportionately, or otherwise. The power changing unit can be configured as separate units to respectively control the energy level of the proton beam and power setting provided to the beamline, respectively, or the power changing unit can be configured as a combined unit. The power changing unit can be a solid state power changing unit or other known or later developed power changing device or switching device configured to include a triggering unit or other feedback unit configured to change the power setting delivered to the beamline magnets according to changes that occur in the energy level of the proton beam being directed through the beamline. The power changing unit can be constructed using sound engineering judgment to achieve the desired results, including, for example, appropriate electrical, solid state, optical, thermal, and/or mechanical relay or detector componentry configured to facilitate changing of the power setting delivered to the beamline according to changes made in the energy level of the proton beam being directed through the beamline. The power changing unit can be operated manually (e.g., with operator assistance) or automatically.

Various example embodiments of the present general inventive concept provide a superconducting proton therapy system that allows a range of energy levels of a proton therapy beam to be delivered at static beamline settings. Other various example embodiments of the present general inventive concept provide a proton delivery system that allows an energy acceptance window, in which the range of different energy levels of a proton therapy beam would otherwise be allowed without changing the beamline settings, to be incrementally changed to approximate the change in depth of the proton therapy.

Numerous variations, modifications, and additional embodiments are possible, and accordingly, all such variations, modifications, and embodiments are to be regarded as being within the spirit and scope of the present general inventive concept. For example, regardless of the content of any portion of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated.

It is noted that the simplified diagrams and drawings included in the present application do not illustrate all the various connections and assemblies of the various components, however, those skilled in the art will understand how to implement such connections and assemblies, based on the illustrated components, figures, and descriptions provided herein, using sound engineering judgment. Numerous variations, modification, and additional embodiments are possible, and, accordingly, all such variations, modifications, and embodiments are to be regarded as being within the spirit and scope of the present general inventive concept.

While the present general inventive concept has been illustrated by description of several example embodiments, and while the illustrative embodiments have been described in detail, it is not the intention of the applicant to restrict or in any way limit the scope of the general inventive concept to such descriptions and illustrations. Instead, the descriptions, drawings, and claims herein are to be regarded as illustrative in nature, and not as restrictive, and additional embodiments will readily appear to those skilled in the art upon reading the above description and drawings. Additional modifications will readily appear to those skilled in the art. Accordingly, departures may be made from such details without departing from the spirit or scope of applicant's general inventive concept.

The invention claimed is:

1. A proton beam delivery system for use in proton therapy, comprising:
    at least one achromatic beamline having a first power setting to direct a proton beam having a first predetermined range of proton beam energies to a target treatment area, a second power setting to direct a proton beam having a second predetermined range of proton beam energies to the target treatment area, and a third power setting to direct a proton beam having a third predetermined range of proton beam energies to the target treatment area; and
    a power changing unit configured to control an energy level of the proton beam and a power setting of the at least one achromatic beamline such that the power changing unit changes the power setting of the at least one achromatic beamline between the first power setting and the second power setting based on changes in proton beam energy that occur within the first predetermined range of proton beam energies, and to incrementally change the power setting of the at least one achromatic beamline between the second and third power settings based on changes on proton beam energy that occur within the second predetermined range of proton beam energies.

2. The system of claim 1, wherein the power changing unit is configured to change the power setting of the at least one achromatic beamline to reach the second power setting as the proton beam energy transitions from the first predetermined range of proton beam energies to the second predetermined range of proton beam energies.

3. The system of claim 1, wherein the power changing unit is configured to change the power setting of the at least one achromatic beamline between the first power setting and the second power setting based on a rate of change of the proton beam energy.

4. The system of claim 1, wherein the power changing unit changes the power setting of the at least one achromatic beamline while the proton beam energy is constant within the first predetermined range of proton beam energies.

5. The system of claim 1, wherein the power changing unit changes the power setting of the at least one achromatic beamline simultaneously with a change in the proton beam energy within the first predetermined range of proton beam energies.

6. The system of claim 1, wherein the first and second predetermined ranges of proton beam energies are mutually distinct and non-inclusive of one another.

7. A method of delivering a proton beam to a patient in a proton therapy system, the method comprising:
    utilizing an achromatic beamline having a first power setting to direct a proton beam having a first predetermined range of proton beam energies to a target treatment area of a patient, a second power setting to direct a proton beam having a second predetermined range of proton beam energies to the target treatment area, and a third power setting to direct a proton beam having a third predetermined range of porton beam energies to the target treatment area;

changing the energy level of the proton beam between the first and second predetermined ranges of proton beam energies;

changing the power setting of the achromatic beamline between the first power setting and the second power setting based on changes in proton beam energy that occur within the first predetermined range of proton beam energies; and changing the power setting of the achromatic beamline between the second and third power setting based on changes in the proton beam energy that occur within the second predetermined range of proton beam energies.

8. The method of claim 7, further comprising changing the power setting of the achromatic beamline to the second power setting as the proton beam energy transitions from the first predetermined range of proton beam energies to the second predetermined range of proton beam energies.

9. The method of claim 7, wherein the incrementally changing the power setting of the achromatic beamline is based on a rate of change of the proton beam energy.

* * * * *